United States Patent [19]
Bounine et al.

[11] Patent Number: 5,994,338
[45] Date of Patent: Nov. 30, 1999

[54] STABILIZED PHARMACEUTICAL COMPOSITIONS, WITH QUINUPRISTINE AND DALFOPRISTINE BASE AND THEIR PREPARATION

[75] Inventors: Jean-Paul Bounine, Maisons Alfort; Guillaume Conrath, Chatenay Malabry, both of France

[73] Assignee: Rhone Poulenc Rorer S.A., Antony, France

[21] Appl. No.: 09/314,070

[22] Filed: May 19, 1999

Related U.S. Application Data

[63] Continuation of application No. PCT/FR97/02047, Nov. 14, 1997.

[30] Foreign Application Priority Data

Nov. 19, 1996 [FR] France .................................. 96 14062

[51] Int. Cl.⁶ .................................................. A61K 31/33
[52] U.S. Cl. ........................................................ 514/183
[58] Field of Search .............................................. 514/183

[56] References Cited

U.S. PATENT DOCUMENTS 4,590,004  5/1986  Corbet et al. ............................. 530/317
4,798,827  1/1989  Barriere et al. .......................... 514/183

OTHER PUBLICATIONS

"Pharmacokinetics and Suction Blister Fluid Penetration of a Semisynthetic Injectable Streptogramin RP 59500 (RP 57669/RP 54476)," *European Journal of Clinical Microbiology & Infectious Diseases*, vol. 13, No. 9 (Sep. 1994).
International Search Report for PCT/FR97/02047 (Mailed Mar. 11, 1998).

*Primary Examiner*—Raymond Henley, III
*Attorney, Agent, or Firm*—Finnegan, Henderson, Farabow, Garrett & Dunner, L.L.P.

[57] ABSTRACT

A stabilized pharmaceutical composition having a combined quinupristine/dalfopristine base and containing an at least stoichiometric amount of methanesulphonic acid or hydrochloric acid and being characterized in that its pH ranges from about 3.5 to about 5. Methods of making and using the stabilized composition are also disclosed.

37 Claims, No Drawings

STABILIZED PHARMACEUTICAL COMPOSITIONS, WITH QUINUPRISTINE AND DALFOPRISTINE BASE AND THEIR PREPARATION

This application is a continuation application of International Application PCT/FR97/02047, filed Nov. 14, 1997.

The present invention relates to stabilized pharmaceutical compositions intended for the parenteral administration of quinupristine and of dalfopristine components of Synercid®.

A description has been given in Patent Application EP 248,703 of pristinamycin I derivatives of general formula:

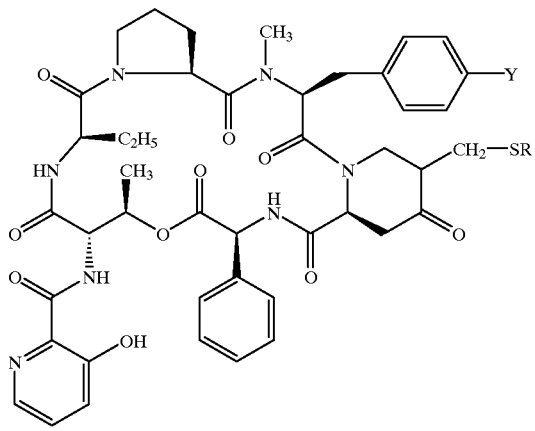

and of their combinations with pristinamycin II derivatives of structure:

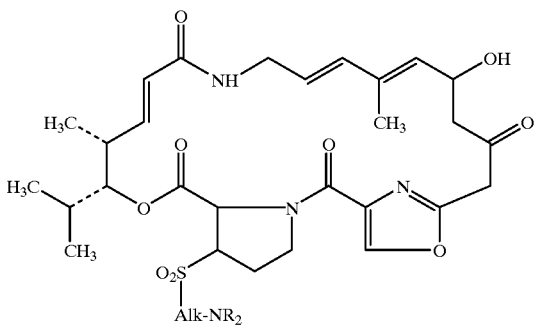

Quinupristine, a derivative of pristinamycin I, and dalfopristine, a derivative of pristinamycin II, are the components of Synercid®:

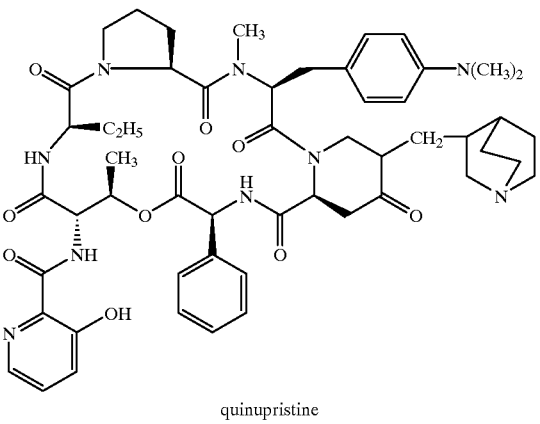

quinupristine

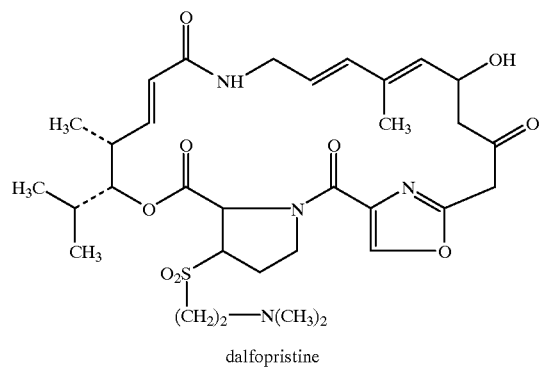

dalfopristine

Synercid® (quinupristine/dalfopristine) is an injectable 30/70 combination, the antibacterial activity of which, in particular with respect to vancomycin-resistant germs, is cited in numerous publications [The Annals of Pharmacotherapy, 29, 1022–1026 (1995); Microbial Drug Resistance, 1, 223–234 (1995)].

The solubilization of the isolated components quinupristine or dalfopristine can be obtained in the salt state.

However, the fact of having to dissolve a combination poses numerous problems, in particular the problem of finding a salifying agent capable of being suitable for each of the components. Moreover, it is necessary to make sure that the pharmaceutical composition exhibits a stability such that the dosage of active principle initially fixed is constant during the lifetime of the medicament. The constitution of stabilized pharmaceutical compositions comprising the quinupristine/dalfopristine combination, the stability of solutions and/or of lyophilisates prepared from solutions, have posed serious problems of preparation which can bring into question the possibility of using them to make a medicament which can be stored and thus marketed. This is due in particular to the significant appearance of degradation impurities.

It has now been found that it is possible to stabilize pharmaceutical compositions comprising the quinupristine/dalfopristine combination by use of at least stoichiometric amounts of methanesulphonic acid or of hydrochloric acid, at a pH within the range [3.5; 5]. Thus, solutions based on methanesulphonic or hydrochloric acid having a pH in the range [3.5; 5] are sufficiently stable for the production of an industrial preparation and result, depending on the situation, in lyophilisates, in reconstituted solutions after lyophilization and/or in frozen solutions which are stable and thus storable with a view to marketing and/or a therapeutic use.

The stabilized pharmaceutical compositions according to the invention are in particular aqueous solutions comprising:

dalfopristine and quinupristine; methanesulphonic or hydrochloric acid, in an at least stoichiometric amount with respect to the sum of the dalfopristine and of the quinupristine introduced;

if necessary, an excess of methanesulphonic or hydrochloric acid intended to adjust the pH of the solution thus formed in the range [3.5; 5];

optionally, an isotonizing agent and/or other pharmaceutically acceptable adjuvants;

an amount of water suitable for adjusting the concentration of the solution.

The solutions thus obtained exhibit the advantage of being stabilized.

According to another aspect of the invention, they can be lyophilized by application of the usual techniques, after lowering the temperature and removing the water. They can be taken up again in water at the time of injection. According to yet another aspect of the invention, they can also be frozen.

When the composition obtained is lyophilized, the latter can be taken up in solution again at the time of use in any compatible and pharmaceutically acceptable injectable medium. The lyophilisate can advantageously be taken up again, for example, in water for injectable preparations or in infusion solutions (glucose solution or sodium chloride, in particular). When the solution has been frozen (frozen bag, for example), it can be defrosted at the time of use. In another alternative, the lyophilisates can also be taken up again in dilute solution (preferably containing less than 20 mg/ml of active principle), the said solution being stored until the time of use.

It is understood that the present invention can also be applied to other soluble pristinamycin derivatives. For example, it can also be applied to derivatives as described in European Patents EP 133,097, EP 135,410, EP 191,662 and EP 248,703 the disclosures of which are herein incorporated by reference.

The stabilized pharmaceutical compositions according to the invention preferably contain concentrations of quinupristine/dalfopristine active principle of between 5 and 250 mg/ml or, in the case of a lyophilisate, in proportions of between 5 and 95%, a proportion of 20 to 90% being more preferred. It is clearly understood that stabilized pharmaceutical compositions of lower concentration can also be produced and clinically used; these solutions also come within the scope of the present invention.

The amount of acid depends on the amount of dalfopristine and quinupristine. It is determined so as to have at least stoichiometric proportions and in such a way as to obtain solutions for which the pH is within the range [3.5; 5].

According to a preferred aspect of the invention, the pH of the starting solution is fixed in a range of [3.5; 4.5], preferably 3.5.

According to another preferred aspect of the invention, in the case of a lyophilized composition, the pH of the solution to be lyophilized is fixed in a range of [4.5; 5].

When the stabilized pharmaceutical compositions according to the invention contain a pharmaceutically acceptable adjuvant, the latter can be chosen, for example, from cosolvents, stabilizers, cryoprotective agents, desiccating agents, fillers and isotonizing agents.

Without implied limitation, the cosolvents and the solubilizing agents can be chosen from polyethylene glycols (polyethylene glycols 300 and 400), propylene glycol, ethanol and surface-active agents, such as, for example, polysorbate 80 or polyoxyethylenated derivatives (cremophors); the fillers and the cryoprotective agents can in particular be chosen from simple sugars (for example glucose, mannitol, fructose or sorbitol), disaccharides (for example sucrose, lactose, trehalose or maltose) or water-soluble polymers (for example dextrans, carboxymethylcellulose, polyvinylpyrrolidone or gelatin); the stabilizing agents can in particular be chosen from antioxidizing agents, and the like; the isotonizing agents can in particular be chosen from glucose, sodium chloride, glycerol, sorbitol, mannitol, fructose or dextrans 40 and 70. When the pH of the solution is high (pH=5 or in the region of 5), if it is desired to prepare a concentrated solution, it is preferable to choose an isotonizing agent other than sodium chloride.

The stabilized pharmaceutical compositions according to the invention are more especially intended for administration by the parenteral route. They can also be used by the oral, ocular or auricular route or in local application on the skin and mucous membranes.

The stabilized pharmaceutical compositions according to the invention are prepared by simultaneously or successively dissolving quinupristine, dalfopristine, methanesulphonic acid or hydrochloric acid in water and then adjusting the pH in the range [3.5; 5] and/or adding an isotonizing agent and/or adding other pharmaceutically acceptable adjuvants and, if appropriate, lyophilizing and/or freezing.

According to a preferred aspect, the compositions according to the invention are prepared by dissolving the quinupristine component and then the dalfopristine component in water acidified by methanesulphonic acid or hydrochloric acid, followed, if appropriate, by the adjustment of the pH in the range [3.5; 5] and/or by the addition of an isotonizing agent and/or of other pharmaceutically acceptable adjuvants. They are, if appropriate, lyophilized and/or frozen.

The solution is generally prepared and divided up from 0° C. to room temperature, preferably at low temperatures, this temperature depending on the duration of the preparation and on the pH. The operations are carried out in particular at a temperature of less than 10° C.

The stabilized pharmaceutical compositions according to the invention can optionally be sterilized. Sterilization is advantageously carried out by sterilizing filtration.

The stabilized pharmaceutical compositions according to the invention, in the liquid, lyophilized or frozen state, exhibit the advantage of an optimum physicochemical stability which makes possible preservation for a period of time which is sufficient for them to be used to prepare a medicament which can be stored and thus marketed.

According to a preferred aspect of the invention, stabilized pharmaceutical compositions is understood to mean compositions exhibiting not more than:

2.0% increase in the level of each of the major degradation impurities (A and B) after preservation for 24 months at 4° C. or for 12 months at 20° C., in the case of a lyophilisate, 2.0% increase in the level of each of the major degradation impurities (A and B) after preservation for 18 hours between 0 and 6° C., in the case of concentrated solutions before or after lyophilization, 2.0 increase in the level of each of the major degradation impurities (A and B) after preservation for 3 months at −20° C., in the case of a frozen composition, 5% increase in the level of each of the major degradation impurities (A and B) after preservation for 6 hours at room temperature or for 72 hours at 4° C., in the case of dilute solutions for infusion.

The following examples, given without implied limitation, illustrate the present invention.

EXAMPLE 1

One litre of a 125 mg/ml solution of quinupristine/dalfopristine (30/70), salified by methanesulphonic acid ($\approx$16.7 mg/ml), at a pH of 4.75, is prepared by introducing 810 g of water for injectable preparations into a dissolution vessel equipped with a cooling unit. The solution is cooled at a temperature of between 0 and 6° C. throughout the manufacturing. 16.4 g of methanesulphonic acid are added and then 37.5 g of quinupristine, which are dissolved by mechanical stirring, and 87.5 g of dalfopristine, which are also dissolved by mechanical stirring, are successively introduced. The pH of the solution is adjusted to 4.75 by a 1N methanesulphonic acid solution. The solution is made up to 1 litre (1030 g) with water for injectable preparations.

This solution is sterilized by sterilized filtration (0.22 $\mu$m) and divided up into bottles [500 mg of quinupristine/dalfopristine (30/70) per bottle] and then lyophilized [freezing: temperature−30° C. to −50° C.; freezing rate approximately 0.5°/min; sublimation: pressure 0.5 mbar; secondary desiccation: pressure ($\approx$30 $\mu$bars) temperature 40° C.].

The quality and the stability during storage of the lyophilisates or of the reconstituted solution are evaluated by a reverse-phase high performance liquid chromatography (HPLC) method which makes it possible to determine the content of dalfopristine and quinupristine and the content of degradation impurities.

HPLC analysis:

| | |
|---|---|
| Stationary phase | Octadecylsilane-grafted silicon, Lichrospher-100 RP18, 5 μm |
| Detection | 254 nm U.V. |
| Dimensions of the column | 125 × 4 mm |
| Temperature of the column | 40° C. |
| Mobile phase A | Phosphate buffer pH 2.9 . . . 80 V Acetonitrile . . . 20 V |
| Mobile phase B | Phosphate buffer pH 2.9 . . . 35 V Acetonitrile . . . 65 V |
| Gradient | from 0% mobile phase B to 66% mobile phase B over 42.5 min, followed by a return to 0% mobile phase B over 1.5 min and re-equilibrating for 5 min |
| Flow rate of the mobile phase | 1.1 ml/min |

The method of analysis by HPLC makes it possible to determine the contents of quinupristine and dalfopristine with an accuracy of 2% and the degradation impurities are determined to within about 0.1%.

Two lyophilized batches of quinupristine/dalfopristine (30/70), composed of bottles containing 500 mg of active principle (batch 1a and batch 1b), were manufactured according to the above process and their stability studied at 4° C. during storage for a period of 2 years. The results of the stability study on each of these 2 batches shows good preservation of the assays of the active principles and very little degradation (see Tables I and II).

Quinupristine/dalfopristine (30/70) solutions are reconstituted from these lyophilisates by taking up again in 5.0 ml of 5% glucose. Under these conditions, the stability of the concentrated solution thus constituted (premix), studied over a period of 60 minutes, is judged largely satisfactory for allowing subsequent dilution in an infusion bag (see Table III).

Under the dilution conditions anticipated for a clinical administration (500 mg of quinupristine/dalfopristine (30/70) in a 250 ml bag containing 5% glucose), the formulation ensures satisfactory stability over a period of at least 72 hours at 4° C. or 6 hours at 25° C. (see Tables IV and V).

Stability results for the lyophilisates over 2 years:

Stability study on batch 1a over a period of 24 months at 4° C.

Stability study on batch 1b over a period of 24 months at 4° C.

TABLE II

| Batch 1b | T0 | 6 months | 9 months | 12 months | 18 months | 24 months |
|---|---|---|---|---|---|---|
| Assay (mg/bottle) | | | | | | |
| Dalfopristine | 349 | 340 | 343 | 343 | 340 | 340 |
| Quinupristine | 148 | 144 | 146 | 142 | 143 | 142 |
| % impurities | | | | | | |
| (A) | 1.0 | 0.8 | 0.8 | 0.9 | 0.9 | 0.8 |
| (B) | 0.5 | 0.6 | 0.4 | 0.6 | 0.4 | 0.5 |
| (C) | 0.2 | 0.2 | 0.1 | 0.2 | 0.1 | 0.2 |
| (D) | 0.4 | 0.4 | 0.4 | 0.4 | 0.4 | 0.3 |
| (E) | 0.1 | — | 0.2 | 0.2 | 0.2 | 0.1 |

Stability results for the concentrated solution reconstituted from lyophilisates (premix):

TABLE III

| Premix | T0 | 15 min | 30 min | 45 min | 60 min |
|---|---|---|---|---|---|
| Assay (% with respect to T0) | | | | | |
| Dalfopristine | 100.0 | 99.7 | 100.2 | 99.0 | 99.0 |
| Quinupristine | 100.0 | 100.2 | 100.7 | 99.6 | 101.1 |
| % impurities | | | | | |
| (A) | 0.74 | 0.89 | 1.02 | 1.12 | 1.28 |
| (B) | 0.51 | 0.62 | 0.69 | 0.72 | 0.78 |
| (D) | 0.47 | 0.49 | 0.46 | 0.53 | 0.61 |
| Sum of the other impurities | 0.28 | 0.30 | 0.32 | 0.33 | 0.38 |

Stability results for the solutions for infusion:

Three batches of lyophilisates manufactured as described above (batch 1c, batch 1d, batch 1e) were used to test the stability of solutions diluted under clinical conditions (500 mg of lyophilized quinupristine/dalfopristine (30/70) diluted in 250 ml of 5% glucose).

Stability of dilute solutions for infusion over a period of 72 hours at 4° C.

TABLE I

| Batch 1a | T0 | 3 months | 6 months | 9 months | 12 months | 18 months | 24 months |
|---|---|---|---|---|---|---|---|
| Assay (mg/bottle) | | | | | | | |
| Dalfopristine | 350 | 347 | 343 | 343 | 345 | 358 | 342 |
| Quinupristine | 149 | 146 | 147 | 149 | 145 | 153 | 144 |
| % impurities | | | | | | | |
| (A) | 1.0 | 1.0 | 1.0 | 0.9 | 0.9 | 1.0 | 0.8 |
| (B) | 0.5 | 0.6 | 0.7 | 0.4 | 0.6 | 0.6 | 0.5 |
| (C) | 0.2 | 0.1 | 0.2 | 0.1 | 0.1 | 0.1 | 0.1 |
| (D) | 0.5 | 0.5 | 0.5 | 0.4 | 0.4 | 0.5 | 0.3 |
| (E) | 0.3 | 0.2 | — | 0.1 | 0.2 | 0.1 | 0.1 |

TABLE IV

| Batches tested | Batch 1c | | Batch 1d | | Batch 1e | |
|---|---|---|---|---|---|---|
| | T0 | 72 h at 4° C. | T0 | 72 h at 4° C. | T0 | 72 h at 4° C. |
| (mg/250 ml) | | | | | | |
| Dalfopristine | 313 | 297 | 314 | 301 | 318 | 306 |
| Quinupristine | 135 | 127 | 134 | 129 | 136 | 131 |
| % impurities | | | | | | |
| (A) | 1.5 | 4.2 | 1.1 | 4.1 | 1.6 | 4.5 |
| (B) | 0.7 | 0.9 | 0.6 | 0.8 | 0.8 | 1.0 |
| (C) | 0.2 | 0.3 | 0.1 | 0.3 | 0.2 | 0.3 |
| (D) | 0.3 | 0.4 | 0.4 | 0.5 | 0.4 | 0.4 |
| (E) | 0.3 | 0.3 | 0.2 | 0.2 | 0.6 | 0.3 |

Stability of dilute solutions for infusion over a period of 6 hours at room temperature

TABLE V

| Batches tested | Batch 1c | | Batch 1d | | Batch 1e | |
|---|---|---|---|---|---|---|
| | T0 | 6 h at room temperature | T0 | 6 h at room temperature | T0 | 6 h at room temperature |
| (mg/250 ml) | | | | | | |
| Dalfopristine | 314 | 304 | 321 | 311 | 319 | 313 |
| Quinupristine | 134 | 132 | 137 | 136 | 137 | 136 |
| % impurities | | | | | | |
| (A) | 1.3 | 4.5 | 1.1 | 4.2 | 1.7 | 4.7 |
| (B) | 0.7 | 0.8 | 0.6 | 0.7 | 0.6 | 0.7 |
| (C) | 0.2 | 0.5 | 0.2 | 0.4 | 0.2 | 0.5 |
| (D) | 0.2 | 0.3 | 0.3 | 0.4 | 0.2 | 0.3 |
| (E) | 0.3 | 0.3 | 0.2 | 0.2 | 0.3 | 0.3 |

EXAMPLE 2

125 mg/ml solutions of quinupristine/dalfopristine (30/70), at a pH of 4.50, salified either by hydrochloric acid or by methanesulphonic acid, are prepared according to the following protocol:

350 g of water for injectable preparations are introduced into a dissolution beaker. 30.0 g of quinupristine are dispersed in the water at room temperature using a mechanical stirrer. A 1N solution of methanesulphonic acid or of hydrochloric acid is added until dissolution is complete and a pH of 4.50 has been obtained. 70.0 g of dalfopristine are dispersed in the water using a mechanical stirrer and then a 1N solution of methanesulphonic acid or of hydrochloric acid is added until dissolution is complete and a pH of 4.50 has been obtained. Homogenization is carried out for 10 minutes.

The solution is made up to 0.8 litre (824 g) with water for injectable preparations.

The lyophilization of this solution according to the protocol described in Example 1 makes it possible to obtain lyophilisates with a satisfactory stability during storage. A stability study in the course of storage at 4° C. and at room temperature (RT) confirms the good stability of the formulations (cf. Tables VI and VII).

Stability of lyophilisates based on methanesulphonic acid over a period of 1 year at 4° C. and at room temperature:

TABLE VI

| Methane-sulphonic acid | T0 | 6 months | | 9 months | | 1 year | |
|---|---|---|---|---|---|---|---|
| | | 4° C. | R.T. | 4° C. | R.T. | 4° C. | R.T. |
| Assay | | | | | | | |
| (mg/bottle) | | | | | | | |
| Dalfopristine | 332 | 322 | 299 | 328 | 319 | 324 | 310 |
| Quinupristine | 143 | 150 | 135 | 149 | 145 | 146 | 143 |
| % impurities | | | | | | | |
| (A) | 3.7 | 4.0 | 3.9 | 3.4 | 3.3 | 4.3 | 4.4 |
| (B) | 1.9 | 1.7 | 1.7 | 1.6 | 2.2 | 1.9 | 2.8 |
| (C) | 0.3 | 0.5 | 0.9 | 0.3 | 0.3 | 0.3 | 0.3 |
| (D) | 1.4 | 1.4 | 1.5 | 1.2 | 1.2 | 1.4 | 1.4 |

Stability of lyophilisates based on hydrochloric acid over a period of 6 months at 4° C. and at room temperature:

TABLE VII

| Hydrochloric acid | T0 | 6 months 4° C. | R.T. |
|---|---|---|---|
| Assay (mg/bottle) | | | |
| Dalfopristine | 327 | 333 | 313 |
| Quinupristine | 156 | 150 | 145 |
| % impurities | | | |
| (A) | 1.7 | 1.6 | 1.4 |
| (B) | 1.6 | 1.6 | 2.4 |
| (C) | 0.3 | 0.2 | 0.2 |
| (D) | 0.9 | 0.4 | 0.4 |

EXAMPLE 3

125 mg/ml solutions of quinupristine/dalfopristine (30/70) are prepared respectively according to Example 1 or 2 at various pH values by addition of a variable amount of 1N methanesulphonic acid; these solutions are intended for lyophilization or for freezing. The pH of the solutions for lyophilization is fixed in a range of between 4.5 and 4.8. The pH of the solutions intended for freezing is fixed in a range of between 3.5 and 4.5.

The stability study on the batches of lyophilisates (prepared under the conditions for dissolution of the active principles described in Example 1 but on a scale of 600 ml, by introducing 150 ml of water and 35 to 50 ml of a 1N solution of methanesulphonic acid before dispersion of the active principles) shows, over a period of 4 years, an optimum stability (see Table VIII).

Stability of lyophilisates in a pH range from 4.3 to 4.8 over a period of 4 years at 4° C.

TABLE VIII

| | Batch 3a pH = 4.3 | | Batch 3b pH = 4.5 | | Batch 3c* pH = 4.7 | | Batch 3d pH = 4.8 | |
|---|---|---|---|---|---|---|---|---|
| | T0 | 4 years 4° C. | T0 | 4 years 4° C. | T0 | 4 years 4° C. | T0 | 4 years 4° C. |
| Assay (mg/bottle) | | | | | | | | |
| Quinupristine | 175 | 148 | 159 | 154 | 152 | 153 | 159 | 149 |
| Dalfopristine | 384 | 291 | 343 | 313 | 331 | 321 | 351 | 328 |
| % impurities | | | | | | | | |
| (A) | 0.6 | 0.5 | 0.6 | 0.8 | 0.8 | 0.9 | 1.1 | 1.1 |
| (B) | 1.0 | 3.3 | 0.8 | 2.1 | 0.9 | 1.2 | 1.0 | 1.1 |
| (C) | 0.5 | 0.5 | 0.4 | 0.4 | 0.4 | 0.4 | 0.3 | 0.5 |
| (D) | 0.8 | 0.7 | 0.9 | 0.6 | 0.7 | 0.6 | 0.8 | 0.5 |

*batch prepared with adjustment of the pH by addition of 6.5 ml of 0.5 N NaOH (under the conditions described below in Example 5).

Stability of solutions intended for freezing, during manufacture, under the conditions of Example 2 (Table IX):

Analysis after dissolution of the active principles, after filtration and before freezing.

TABLE IX

| | Solution pH 3.5 Batch 3e | | | Solution pH 4.0 Batch 3f | | | Solution pH 4.5 Batch 3g | | |
|---|---|---|---|---|---|---|---|---|---|
| | (1) | (2) | (3) | (1) | (2) | (3) | (1) | (2) | (3) |
| Assay (mg/bottle) | | | | | | | | | |
| Quinupristine | 147 | 148 | 152 | 147 | 153 | 148 | 144 | 136 | 144 |
| Dalfopristine | 339 | 328 | 335 | 320 | 336 | 331 | 334 | 313 | 334 |
| % impurities | | | | | | | | | |
| (A) | 2.0 | 1.9 | 2.0 | 1.8 | 1.8 | 2.0 | 2.6 | 3.3 | 3.6 |

TABLE IX-continued

|  | Solution pH 3.5 Batch 3e | | | Solution pH 4.0 Batch 3f | | | Solution pH 4.5 Batch 3g | | |
|---|---|---|---|---|---|---|---|---|---|
|  | (1) | (2) | (3) | (1) | (2) | (3) | (1) | (2) | (3) |
| (B) | 0.9 | 1.1 | 1.3 | 1.0 | 1.0 | 1.6 | 1.0 | 1.5 | 1.7 |
| (C) | 0.3 | 0.3 | 0.3 | 0.3 | 0.4 | 0.4 | 0.2 | 0.4 | 0.2 |
| (D) | 0.9 | 1.0 | 1.1 | 1.1 | 1.0 | 1.0 | 1.4 | 1.4 | 1.4 |

(1): After dissolution
(2): After filtration
(3): Before freezing

EXAMPLE 4

Quinupristine/dalfopristine (30/70) solutions at a pH of 4.75 and at various concentrations of between 125 mg/ml and 250 mg/ml are prepared according to Example 1. These solutions are used to produce 500 mg lyophilisates. The most concentrated solutions (200 and 250 mg/ml) are slower to employ because of the time for dissolution of the dalfopristine and of the period of time for adjustment of the pH. The study shows that the degradation profiles during manufacture are not modified, only the times for redissolving lyophilisates are increased when the concentration of the solution is increased (see Table X).

Degradation profile for solutions during manufacture (after filtration and after lyophilization)

Conditions for redissolving the lyophilisates.

TABLE X

|  | Batch 4a 125 mg/ml | | Batch 4b 143 mg/ml | | Batch 4c 167 mg/ml | | Batch 4d 200 mg/ml | | Batch 4e 250 mg/ml | |
|---|---|---|---|---|---|---|---|---|---|---|
|  | (1) | (2) | (1) | (2) | (1) | (2) | (1) | (2) | (1) | (2) |
| % impurities | | | | | | | | | | |
| (A) | 1.10 | 0.99 | 0.66 | 1.13 | 0.58 | 0.74 | 0.54 | 0.58 | 0.38 | 0.56 |
| (B) | 0.78 | 0.83 | 0.61 | 0.92 | 0.58 | 0.72 | 0.65 | 0.76 | 0.52 | 0.80 |
| (C) | 0.26 | 0.25 | 0.24 | 0.28 | 0.24 | 0.29 | 0.25 | 0.26 | 0.24 | 0.24 |
| (D) | 0.52 | 0.55 | 0.58 | 0.60 | 0.58 | 0.62 | 0.54 | 0.62 | 0.49 | 0.51 |
| Total known impurities | 2.66 | 2.62 | 2.09 | 2.93 | 1.98 | 2.37 | 1.98 | 2.22 | 1.63 | 2.11 |
| Sum of the unknown impurities | 2.38 | 2.37 | 2.18 | 2.22 | 2.27 | 2.44 | 2.29 | 2.13 | 2.24 | 2.09 |
| Total impurities | 5.04 | 4.99 | 4.27 | 5.15 | 4.25 | 4.81 | 4.27 | 4.35 | 3.87 | 4.20 |
| REDISSOLUTION | | | | | | | | | | |
| Time for redissolving in 4 ml of 5% glucose | — | 40 s | — | 50 s | — | 50 s | — | 2 min 30 s | — | 3 min |
| pH of the solution reconstituted in 4 ml of 5% glucose | — | 4.54 | — | 4.56 | — | 4.56 | — | 4.55 | — | 4.44 |

(1): Solution after filtration
(2): Lyophilisate (T12H)

EXAMPLE 5

125 mg/ml solutions of quinupristine/dalfopristine (30/70) are prepared according to Example 1 for which the adjustment of the pH to 4.75 is carried out by variable amounts of 1N methanesulphonic acid (1 to 9 ml/l) and of 0.5N sodium hydroxide (0 to 15 ml/l).

Conditions for adjustment of the pH (per litre of solution)

TABLE XI

|  | Batch 5a | Batch 5b | Batch 5c | Batch 5d | Batch 5e | Batch 5f |
|---|---|---|---|---|---|---|
| Starting amount of methanesulphonic acid (g/l) | 16.36 | 16.36 | 16.36 | 16.36 | 16.36 | 16.36 |
| Adjustment of the pH: | | | | | | |
| Addition of 1 N methanesulphonic acid (ml/l) | 1.0 | 2.0 | 4.0 | 4.4 | 8.0 | 9.0 |
| Addition of 0.5 N NaOH (ml/l) | 0 | 0 | 7.0 | 6.2 | 15.0 | 14.0 |

The stability of the solutions manufactured (studied at 3° C. over a period of 20 hours) shows no difference according to the conditions for adjustment of the pH.

Stability of the lyophilisates obtained:

TABLE XII

| | Batch 5b | | | | Batch 5d | | | | Batch 5f | | | |
|---|---|---|---|---|---|---|---|---|---|---|---|---|
| | T0 | 4 months 30° C. | 1 month 30° C. | 3 months 30° C. | T0 | 4 months 4° C. | 1 month 30° C. | 3 months 30° C. | T0 | 4 months 4° C. | 1 month 30° C. | 3 months 30° C. |
| Assay (mg/5 ml) | | | | | | | | | | | | |
| Quinupristine | 154.4 | 153.5 | 153.6 | 156.5 | 152.8 | 153.3 | 151.4 | 150.8 | 146.3 | 146.2 | 144.1 | 143.0 |
| Dalfopristine | 361.4 | 364.4 | 358.9 | 354.8 | 358.7 | 359.6 | 353.2 | 345.7 | 345.9 | 347.1 | 340.7 | 336.4 |
| % impurities | | | | | | | | | | | | |
| (A) | 0.88 | 0.73 | 0.88 | 0.81 | 0.83 | 0.76 | 0.85 | 0.78 | 1.00 | 0.91 | 1.01 | 0.96 |
| (B) | 0.51 | 0.45 | 0.77 | 0.91 | 0.49 | 0.53 | 0.86 | 0.98 | 0.60 | 0.58 | 0.84 | 0.98 |
| (C) | 0.23 | 0.14 | 0.22 | 0.27 | 0.26 | 0.20 | 0.29 | 0.26 | 0.24 | 0.17 | 0.22 | 0.25 |
| (D) | 0.40 | 0.35 | 0.45 | 0.46 | 0.34 | 0.34 | 0.39 | 0.40 | 0.39 | 0.33 | 0.33 | 0.39 |
| (E) | 0.16 | 0.15 | 0.19 | 0.17 | 0.16 | 0.15 | 0.17 | 0.16 | 0.21 | 0.19 | 0.22 | 0.21 |

EXAMPLE 6

Frozen quinupristine/dalfopristine (30/70) solutions, salified by methanesulphonic acid or by hydrochloric acid, are prepared in a concentration range of 5 and 20 mg/ml and at pH values of 3.5 and 5.0 and in the presence of isotonizing agents, such as NaCl and glucose. The stability of the solutions stored in the frozen form is judged satisfactory. (a) 800 g of water for injectable preparations are introduced into a dissolution vessel equipped with a cooling unit. The solution is cooled at a temperature of between 0 and 6° C. throughout the manufacture. 98% of the amount of methanesulphonic acid necessary for the dissolution and for the adjustment of the pH are added. 1.5 g of quinupristine are introduced and dissolved with mechanical stirring. 3.5 g of dalfopristine are introduced and dissolved with mechanical stirring. The solution is isotonized with glucose. The pH of the solution is adjusted to 5.0 by a 0.1N solution of methanesulphonic acid. This solution is made up to 1 litre with water for injectable preparations.

Stability of the batch prepared above in (a) during a period of 3 months at −22° C.:

TABLE XIII

| | T0 | 3 months |
|---|---|---|
| Assay (mg/ml) | | |
| Dalfopristine | 3.37 | 3.38 |
| Quinupristine | 1.41 | 1.37 |
| % impurities | | |
| (A) | 2.42 | 2.55 |
| (B) | 0.32 | 0.37 |
| (C) | 0.18 | 0.29 |
| (D) | 0.32 | 0.37 |
| (E) | — | 0.12 |

(b) The preparation is carried out as described above but introducing 6 g of quinupristine and 14 g of dalfopristine. The pH of the solution is adjusted to 3.5 by a 0.1N solution of methanesulphonic acid. The solution is made up to 1 litre with water for injectable preparations.

Stability of the batch prepared above in (b) during a period of 3 months at −22° C.:

TABLE XIV

| | T0 | 3 months |
|---|---|---|
| Assay (mg/ml) | | |
| Dalfopristine | 14.0 | 16.8 |
| Quinupristine | 5.5 | 6.6 |
| % impurities | | |
| (A) | 0.29 | 0.74 |
| (B) | 0.26 | 0.30 |
| (C) | 0.27 | 0.28 |
| (D) | 0.31 | 0.40 |

(c) The preparation is carried out as described above in (a) but isotonizing the solution with sodium chloride and adjusting the pH to 3.5 by a 0.1N solution of methanesulphonic acid. The solution is made up to 1 litre with water for injectable preparations.

Stability of the batch prepared above in (c) during a period of 3 months at −22° C.:

TABLE XV

| | T0 | 3 months |
|---|---|---|
| Assay (mg/ml) | | |
| Dalfopristine | 3.57 | 3.90 |
| Quinupristine | 1.42 | 1.57 |
| % impurities | | |
| (A) | 0.25 | 0.56 |
| (B) | 0.20 | 0.21 |
| (C) | 0.21 | 0.15 |
| (D) | 0.30 | 0.35 |

(d) The preparation is carried out as described above in (c) but adjusting the pH to 5.0 by a 0.1N solution of hydrochloric acid. The solution is made up to 1 litre with water for injectable preparations.

Stability of the batch prepared above in (d) during a period of 3 months at −22° C.:

TABLE XVI

|  | T0 | 3 months |
|---|---|---|
| Assay (mg/ml) | | |
| Dalfopristine | 3.41 | 3.89 |
| Quinupristine | 1.45 | 1.63 |
| % impurities | | |
| (A) | 2.77 | 2.64 |
| (B) | 0.32 | 0.35 |
| (C) | 0.21 | 0.15 |
| (D) | 0.32 | 0.37 |

We claim:

1. A stabilized pharmaceutical composition comprising a pharmaceutically effective amount of quinupristine and dalfopristine, wherein said composition further comprises an at least stoichiometric amount, with respect to the total amount of dalfopristine and quinupristine present in said composition, of at least one acid chosen from methanesulphonic acid and hydrochloric acid, and wherein said composition is physiochemically stable.

2. A stabilized pharmaceutical composition according to claim 1, wherein said stabilized composition is lyophilized, frozen, or in the liquid state.

3. A stabilized pharmaceutical composition according to claim 2, wherein said liquid state comprises a reconstituted solution following lyophilization.

4. A stabilized pharmaceutical composition according to claim 1, wherein said pharmaceutically effective amount of quinupristine and dalfopristine is constant during the lifetime of said composition.

5. A stabilized pharmaceutical composition according to claim 1, wherein said quinupristine and said dalfopristine are present in a ratio of approximately 30:70.

6. A stabilized pharmaceutical composition according to claim 1, wherein any water present in said composition is removed to form a lyophilizate.

7. A stabilized pharmaceutical composition according to claim 1, wherein said pharmaceutically effective amount of quinupristine and dalfopristine ranges from about 5 to about 250 mg/ml.

8. A stabilized pharmaceutical composition according to claim 1, wherein said pharmaceutically effective amount of quinupristine and dalfopristine is less than 5 mg/ml.

9. A stabilized pharmaceutical composition according to claim 6, wherein said pharmaceutically effective amount of quinupristine and dalfopristine in said lyophilizate ranges from about 5 to about 95%, by weight based upon the weight of the lyophilizate.

10. A stabilized pharmaceutical composition according to claim 9, wherein said pharmaceutically effective amount of quinupristine and dalfopristine in said lyophilizate ranges from about 20 to about 90%, by weight based upon the weight of the lyophilizate.

11. A stabilized pharmaceutical composition according to claim 1, wherein the pH of said composition ranges from 3.5 to 5.0.

12. A stabilized pharmaceutical composition according to claim 11, wherein the pH of said composition ranges from 3.5 to 4.5.

13. A stabilized pharmaceutical composition according to claim 12, wherein the pH is about 3.5.

14. A stabilized pharmaceutical composition according to claim 6, wherein the pH ranges from about 4.5 to about 5.

15. A stabilized pharmaceutical composition according to claim 1, said composition further comprising an additional amount of said at least one acid sufficient to adjust the pH of the composition to be within the range of from about 3.5 to about 5.0.

16. A stabilized pharmaceutical composition according to claim 1, further comprising at least one ingredient chosen from isotonizing agents, fillers, cosolvents, stabilizers, cyroprotecting agents, desiccating agents, and other pharmaceutically acceptable adjuvants.

17. A stabilized pharmaceutical composition according to claim 1, wherein when said stabilized composition is in the form of a lyophilizate, said composition does not exhibit more than a 2.0% increase in the amount of each of the two major degradation impurities following preservation for 24 months at 4° C. or for 12 months at 20° C.

18. A stabilized pharmaceutical composition according to claim 1, wherein when said stabilized composition is in the form of a concentrated solution before or after lyophilization, said composition does not exhibit more than a 2.0% increase in the amount of each of the two major degradation impurities following preservation for 18 hours at a temperature ranging from 0 to 6° C.

19. A stabilized pharmaceutical composition according to claim 1, wherein when said stabilized composition is in the form of a frozen composition, said composition does not exhibit more than a 2.0% increase in the amount of each of the two major degradation impurities following preservation for 3 months at −20° C.

20. A stabilized pharmaceutical composition according to claim 1, wherein when said stabilized composition is in the form of a dilute solution for infusion, said composition does not exhibit more than a 5% increase in the amount of each of the two major degradation impurities following preservation for 6 hours at room temperature or for 72 hours at 4° C.

21. A process for preparing a stabilized pharmaceutical composition, said process comprising-simultaneously or successively introducing into water a pharmaceutically effective amount of quinupristine and dalfopristine and an at least stoichiometric amount, with respect to the total amount of quinupristine and dalfopristine present in said composition, of at least one acid chosen from methanesulphonic acid and hydrochloric acid under conditions sufficient to achieve a stabilized pharmaceutical composition.

22. A process for preparing a stablized pharmaceutical composition according to claim 21, said process further comprising adjusting the pH of said composition to be within the range of from 3.5 to 5.0.

23. A process for preparing a stablized pharmaceutical composition according to claim 21, wherein said introducing into water is achieved by dissolving said pharmaceutically effective amount of quinupristine and dalfopristine in said water.

24. A process for preparing a stabilized pharmaceutical composition according to claim 21, said process further comprising lyophilizing and/or freezing said stabilized composition.

25. A process for preparing a stabilized pharmaceutical composition according to claim 21, said process further comprising sterilizing said stabilized compostion.

26. A process for preparing a stabilized pharmaceutical composition, said process comprising successively introducing quinupristine and then dalfopristine into water acidified by at least one acid chosen from methanesulphonic acid and hydrochloric acid under conditions sufficient to achieve a stabilized pharmaceutical composition.

27. A process for preparing a stablized pharmaceutical composition according to claim 26, said process further comprising adjusting the pH of said composition to be within the range of from 3.5 to 5.0.

28. A process for preparing a stabilized pharmaceutical composition according to claim 27, wherein said adjusting of the pH is achieved by at least one acid chosen from methanesulphonic acid and hydrochloric acid.

29. A process for preparing a stabilized pharmaceutical composition according to claim 26, said process further comprising lyophilizing and/or freezing said stabilized composition.

30. A process for preparing a stabilized pharmaceutical composition according to claim 21, said process further comprising including at least one ingredient chosen from isotonizing agents, fillers, cosolvents, stabilizers, cyroprotecting agents, desiccating agents, and other pharmaceutically acceptable adjuvants.

31. A process for preparing a stabilized pharmaceutical composition, said process comprising reconstituting a lyophilizate comprising a pharmaceutically effective amount of quinupristine and dalfopristine, wherein said composition further comprises an at least stoichiometric amount, with respect to the total amount of dalfopristine and quinupristine present in said composition, of at least one acid chosen from methanesulphonic acid and hydrochloric acid, wherein said reconstituting step is carried out under conditions sufficient to provide a physiochemically stable pharmaceutical composition in any compatible and pharmaceutically acceptable injectable medium or infusion solution.

32. A process for preparing a stabilized pharmaceutical composition, said process comprising reconstituting a lyophilizate comprising a pharmaceutically effective amount of quinupristine and dalfopristine, wherein said composition further comprises an at least stoichiometric amount, with respect to the total amount of dalfopristine and quinupristine present in said composition, of at least one acid chosen from methanesulphonic acid and hydrochloric acid, wherein said reconstituting step is carried out under conditions sufficient to provide a physiochemically stable pharmaceutical composition, and wherein said reconstituting step is carried out with a dilute solute having less than 20mg/ml of said quinupristine and dalfopristine.

33. A process for preparing a stabilized pharmaceutical composition, said process comprising defrosting a frozen composition comprising a pharmaceutically effective amount of quinupristine and dalfopristine, wherein said composition further comprises an at least stoichiometric amount, with respect to the total amount of dalfopristine and quinupristine present in said composition, of at least one acid chosen from methanesulphonic acid and hydrochloric acid, wherein said defrosting step is carried out under conditions sufficient to provide a physiochemically stable pharmaceutical composition.

34. A method for treating a bacterial infection, said method comprising administering to a patient in need thereof an effective amount of a stabilized pharmaceutical composition comprising a pharmaceutically effective amount of quinupristine and dalfopristine, wherein said composition further comprises an at least stoichiometric amount, with respect to the total amount of dalfopristine and quinupristine present in said composition, of at least one acid chosen from methanesulphonic acid and hydrochloric acid, and wherein said composition is physiochemically stable.

35. A method of treating a bacterial infection according to claim 34, wherein the bacterial infection is a vancomycin-resistant infection.

36. A method of treating a bacterial infection according to claim 34, wherein the stabilized composition is administered by a parenteral, oral, auricular, or ocular route, or by local application to the skin and/or mucous membranes.

37. A stabilized pharmaceutical composition comprising a pharmaceutically effective amount of a soluble pristinamycin I derivative and a soluble pristinamycin II derivative, wherein said composition further comprises an at least one stoichiometric amount, with respect to the total amount of pristinamycin I derivative and pristinamycin II derivative present in said composition, of at least one acid chosen from methanesulphonic acid and hydrochloric acid, and wherein said composition is physiochemically stable.

* * * * *

UNITED STATES PATENT AND TRADEMARK OFFICE
CERTIFICATE OF CORRECTION

PATENT NO.: 5,994,338                     Page 1 of 2
DATED: November 30, 1999
INVENTOR(S): Bounine et al.

It is certified that an error appears in the above-identified patent and that said Letters Patent is hereby corrected as shown below:

Col. 2, L. 14, change "$N(CH_3)_2$" to --$N(C_2H_5)_2$--.

CLAIM 1, Col. 15, L. 22, change "physiochemically" to --physicochemically--.

CLAIM 21, Col. 16, L. 36, change "comprising-simultaneously" to --comprising simultaneously--.

CLAIM 31, Col. 17, L. 26, change "physiochemically" to --physicochemically--.

CLAIM 32, Col. 17, L. 38, change "physiochemically" to --physicochemically--.

CLAIM 33, Col. 18, L. 10, change "physiochemically" to --physicochemically--.

CLAIM 34, Col. 18, L. 22, change "physiochemically" to --physicochemically--.

UNITED STATES PATENT AND TRADEMARK OFFICE
CERTIFICATE OF CORRECTION

PATENT NO. : 5,994,338
DATED : November 30, 1999
INVENTOR(S) : Bounine et al

It is certified that error appears in the above-identified patent and that said Letters Patent is hereby corrected as shown below:

CLAIM 37, Col. 18, L. 39, change "physiochemically" to --physicochemically--.

Signed and Sealed this

Fourth Day of July, 2000

Attest:

Q. TODD DICKINSON

Attesting Officer      Director of Patents and Trademarks